United States Patent [19]

Inbar et al.

[11] Patent Number: 4,573,122
[45] Date of Patent: Feb. 25, 1986

[54] METHOD OF AND MEANS FOR COMPENSATING FOR THE DEAD TIME OF A GAMMA CAMERA

[75] Inventors: Dan Inbar, Haifa; Alexander Ganin, Kiryat Bialick, both of Israel

[73] Assignee: Elscint, Ltd., Haifa, Israel

[21] Appl. No.: 439,221

[22] Filed: Nov. 4, 1982

Related U.S. Application Data

[63] Continuation of Ser. No. 160,942, Jun. 19, 1980, Pat. No. 4,369,495.

[51] Int. Cl.$^4$ ............................................. G01T 1/20
[52] U.S. Cl. .................................. 364/414; 364/571; 250/363 S
[58] Field of Search .................. 364/414, 527, 571; 358/110, 111; 250/363 S, 363 R

[56] References Cited

U.S. PATENT DOCUMENTS

| | | | |
|---|---|---|---|
| 3,732,420 | 5/1973 | Brunnett et al. | 250/363 S X |
| 4,058,728 | 11/1977 | Nickles | 250/363 S X |
| 4,095,108 | 6/1978 | Imbar et al. | 250/363 S X |
| 4,115,694 | 9/1978 | Lange et al. | 250/363 S |
| 4,179,607 | 12/1979 | Lange et al. | 250/363 S |
| 4,223,221 | 9/1980 | Gambini et al. | 250/363 S |

Primary Examiner—Edward J. Wise
Attorney, Agent, or Firm—Sandler & Greenblum

[57] ABSTRACT

A method for using a gamma camera having a head including an array of photodetectors that produces a group of input pulses in response to an actual interaction of a radiation stimulus with the camera head, includes the step of repetitiously generating groups of synthetic pulses that resemble groups of input pulses and simulate the occurrence of synthetic interactions of stimuli with the head. These groups of synthetic and input pulses are applied to processing circuitry that produces groups of processed pulses. The coordinates of both actual and synthetic interactions based on said processed pulses are computed; and a representation of the spatial locations of both actual and synthetic interactions based on the computed coordinates is stored.

The method also includes determining whether a group of processed pulses is the result of a group of input pulses or a group of synthetic pulses, and a correction factor is computed based on the number of groups of processed synthetic pulses relative to the number of groups of generated synthetic pulses. The representation of the spatial locations of the interactions is corrected in accordance with said correction factor.

16 Claims, 4 Drawing Figures

METHOD OF AND MEANS FOR COMPENSATING FOR THE DEAD TIME OF A GAMMA CAMERA

This is a continuation of application Ser. No. 160,942 filed June 19, 1980 now U.S. Pat. No. 4,369,495.

DESCRIPTION

1. Technical Field

This invention relates to a method of and means for compensating for the dead time losses of a nuclear imaging system such as a gamma camera.

2. Background of Invention

The dead time of a nuclear imaging system is the time during which the system processes a single event (i.e., the interaction of a particle or stimulus from a radiation field with the system) and is not available to process a succeeding event. It arises because of the multitude of electronic circuits in a nuclear imaging system, each with its own dead time, and the complex interaction between such circuits. Furthermore, the count rate losses of a system are a function of the number of particles produced by the radiation field under investigation which lie outside the energy window of the single channel analyzer of the system because the interactions of such particles occupy the circuitry of the system while a decision is being reached with regard to further processing. Thus, the dead time of a nuclear imaging system depends on the nature of the system and the type of field interacting therewith.

As a consequence of the dead time phenomenon in nuclear imaging systems, the rate at which events are processed by the system is a non-linear function of the rate of incoming events. For a typical conventional gamma camera, the curve relating events processed to incoming events peaks at about 200,000 counts per second which defines the so-called foldback point of the curve. At such point, the typical camera processes only about 50% of the incoming events; while at greater counting rates, the efficiency of the camera drops below 50%. Thus, if a radiation field produces particles that interact with the camera at rates in excess of 200,000 per second, less than half of these events will be processed by the camera and appear in a map of the radiation field.

The inherent variable dead time losses in a gamma camera do not significantly degrade images of static radiation fields. For example, it is conventional to obtain an image of an organ such as the liver or thyroid by injecting a patient with a radioactive pharmaceutical that gravitates to the organ of interest and remains there for a relatively long time as compared to the time required to obtain an image of the organ using the nuclear imaging system. In this case, the intensity distribution of counts over an area is desired and the efficiency of the camera in processing events has no significant importance.

However, where physiological dynamic mechanisms are being studied, such as the rate at which blood is washed out of the brain or kidney, or the quantity of blood pumped by the heart in each cycle, the quantity/time behaviour of the incoming events presented to the camera becomes crucial because the quantitative information indicates the degree of abnormality in the function of an organ. For example, a radiopharmaceutical injected into the vascular system of a patient will reach the heart essentially as a substantially undiluted bolus. The initial contraction of the heart will draw this bolus into the heart pool which, as a result will have an activity that will produce, say, 500,000 particles per second that interact with the camera, but only for a few seconds before a portion of the pool is expelled by the contraction of the heart. The radiopharmaceutical remaining in the heart is diluted by the next cycle of the heart, reducing further the radioactivity, and thus reducing the number of events presented to the camera. After five or six contractions, the amount of radiopharmaceutical remaining in the blood pool in the heart is so reduced that coming events to the camera are reduced to, say, 50,000 particles per second.

If the above described process were imaged with a conventional gamma camera uncompensated for its dead time, its inefficiency due to the dead time phenomena would suppress the processing of events in direct proportion to the rate at which these events are presented to the camera. That is to say, the greater the rate of nuclear activity in the heart, the higher the losses in the gamma camera which, as a consequence, would yield distorted data that conceals the true situation. Any diagnosis based on such data is likely to be incorrect.

One approach to compensating for the dead time of a gamma camera in order to take into account the dependency of the efficiency of the camera on the rate of incoming events is to assume an analytical approximation of the statistical probability of an event that encounters an electronic component in the camera will be operated on by such component. As indicated previously, dead time is extremely complicated and is dependent not only on the inherent limitations of the camera itself but on the nuclear spectra which the camera is associated. As a consequence, the use of an analytical function to compensate for dead time yields high error.

It is therefore an object of the present invention to provide a new and improved method of and means for compensating for the dead time of a gamma camera which is less complex than the techniques of the prior art and more likely to produce accurate results.

DISCLOSURE OF INVENTION

In accordance with the present invention, the dead time of a nuclear imaging system is compensated for when mapping a frame of a dynamically changing radiation field into a image memory by injecting into the system synthetic pulses that resemble, in terms of amplitude and shape, pulses produced by the system in response to interaction of stimuli from the radiation field, and by determining the percentage of synthetic pulses processed by the system. A correction factor based on such percentage is applied to each cell of the image memory to correct the resultant map of the radiation field.

The rate at which the synthetic pulses are injected into the system must be high enough to have a sufficient statistical value but low enough so as not to influence the dead time losses. Such rate should be in the range of 3%–10% of the rate of incoming events, and preferably about 5%.

In the preferred embodiment of the invention, the synthetic signals are injected in such a way that relatively low correlation exists between the pulses produced by interactions of stimuli from the radiation field and the synthetic pulses. This is achieved by counting a predetermined number of pulses processed by the system to produce a control signal, delaying the control signal for a time greater than the dead time of the system to produce a trigger signal, and injecting a synthetic pulse into the system in response to the trigger signal.

BRIEF DESCRIPTION OF DRAWINGS

Details of the invention are described in connection with the accompanying drawings wherein.

BEST MODE FOR CARRYING OUT THE INVENTION

Figure 1:
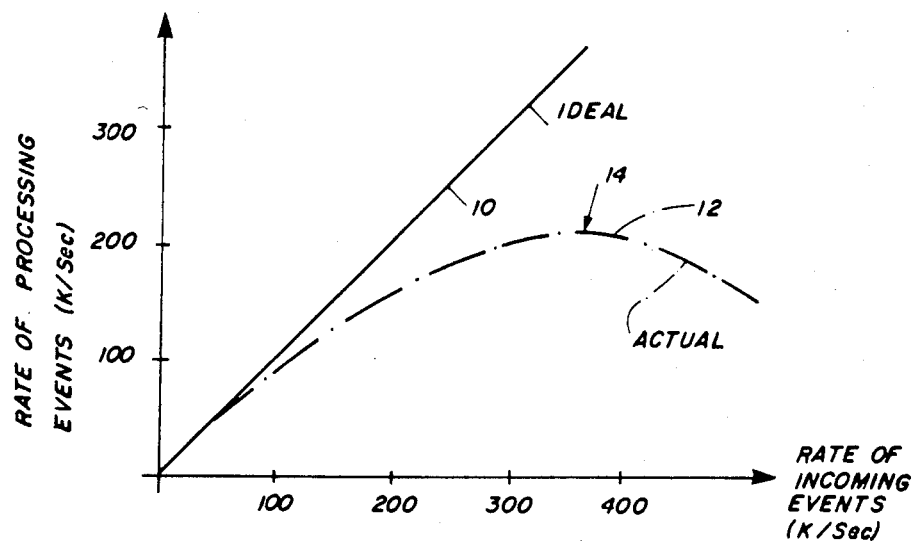
FIG. 1 is a graph showing the ideal and actual relationship between the rate at which events are processed in a typical nuclear imaging system as a function of the rate at which incoming events are presented to the system.

Referring now to FIG. 1, reference numeral 10 designates the ideal relationship between the rate at which events are processed by a nuclear imaging system, as for example a gamma camera, and the rate at which incoming events are applied to the system. As can be seen, the ideal relationship is a linear one with a slope of unity. Curve 12 is typical of the actual relationship between the rate at which events are processed and the rate at which events are applied to the system for a typical gamma camera. As can be seen from curve 12, the camera has an efficiency of about 50% when the rate of incoming events is about 200,000 counts per second; and this efficiency decreases as the rate of incoming events exceeds 200,000 counts per second. The peak value of curve 12 is termed the "foldover" point, and is designated by reference numeral 14.

The difference between curves 10 and 12 arises because of the dead time associated with the gamma camera. The effect that dead time exerts on an image obtained with the gamma camera when the radiation field is dynamic is shown in FIG. 2 to which reference is now made.

Figure 2:
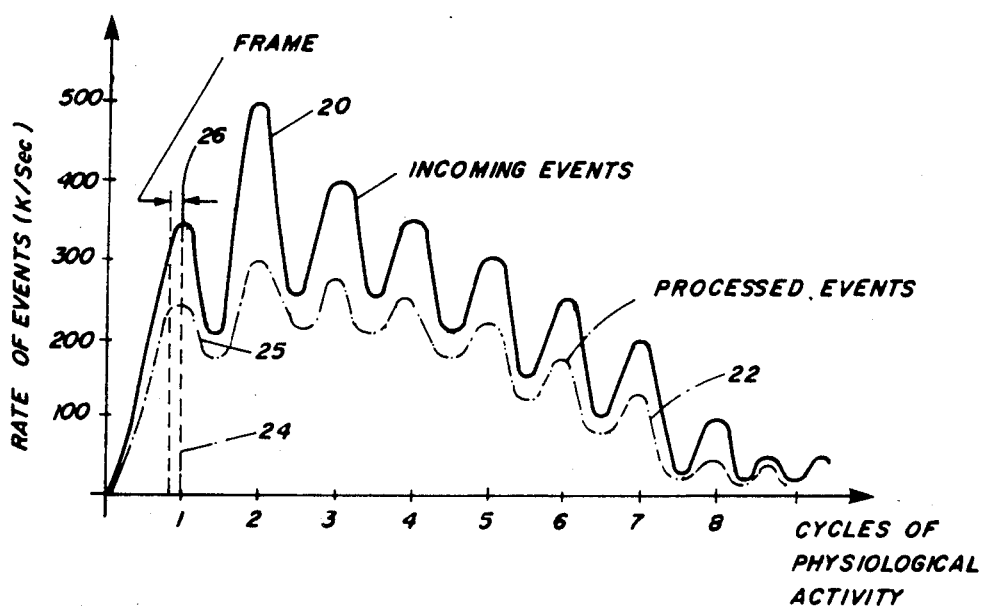
FIG. 2 is a graph showing the relationship between the time variation of incoming events due to a dynamic radiation field presented to a nuclear imaging system, and the time variation of events processed by a conventional nuclear imaging system in order to illustrate how the dead time of the system suppresses the quantitative nature of a radiation field.

Curve 20 in FIG. 2 is typical of the nuclear activity in the blood in the heart pool as a consequence of injection of a radiopharmaceutical into the vascular system of a patient. Over the first five or six contractions of the heart after the dye reaches the heart, nuclear activity within the heart is relatively high because the radiopharmaceutical is not significantly diluted by the blood pool of the body. After these initial contractions, and after about one minute, the dilution becomes more pronounced and the nuclear activity of the blood in the heart decreases significantly.

Experience has shown that the initial nuclear activity due to the quantity of radiopharmaceutical present in a normal heart is in the range of 400,000–500,000 counts per second for about one minute, then the activity drops to around 20,000 counts per second.

Curve 22 represents the output of a gamma camera having a response curve similar to curve 12 shown in FIG. 1. That is to say, the dead time of the camera seriously affects its ability to track the relatively high counting rates at the peak of the physiological activity of a heart. The camera thus cannot follow the rapid excursions in the counting rate. If a single frame such as frame 24 of the radiation field is obtained using the gamma camera having a curve like that shown in FIG. 1, the quantitative information obtained from a map would be seriously in error as indicated by comparing the peak 25 of curve 22 in the frame to the peak 26 of curve 20 in the frame. A diagnosis based on the quantitative information contained in the image would be incorrect by reason of the effect of dead time on the gamma camera.

Figure 3:
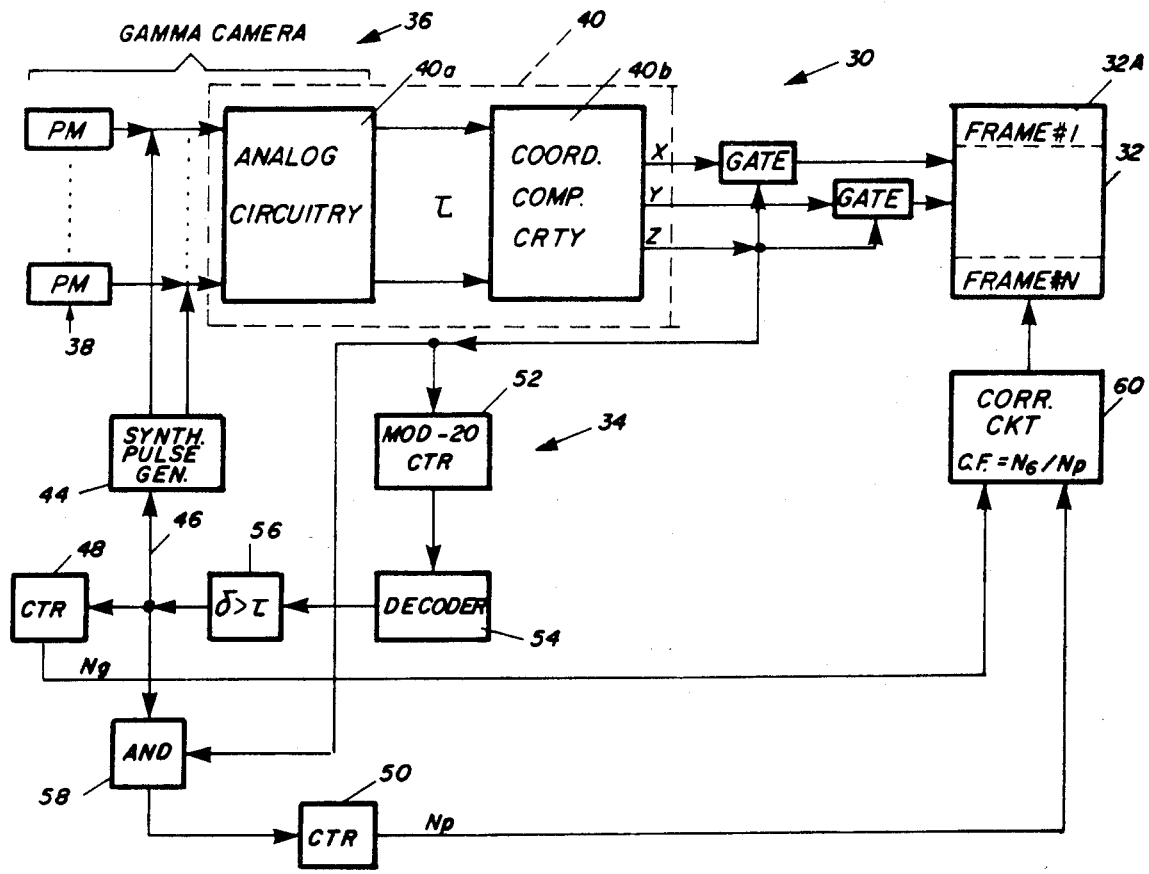
FIG. 3 is a block diagram of a nuclear imaging system provided with means according to the present invention for compensating for the dead time of a gamma camera.

Referring now to FIG. 3, reference numeral 30 designates a nuclear imaging system for mapping a frame of a dynamically changing radiation field into image memory 32, including means 34 according to the present invention for compensating for the dead time of the nuclear imaging system. System 30 includes gamma camera head 36 which comprises a plurality of photomultiplier tubes 38 arranged in a predetermined array with respect to a scintillation crystal (not shown) with which stimuli from a radiation field will interact, thereby producing light events in the crystal and causing the photomultiplier tubes to produce signals, the amplitudes of which are directly related to the relative distance of a light event from the photomultiplier tubes. Light events produced in the scintillation crystal have a distinctive shape characterized by a rapidly rising leading edge and a trailing edge with a time constant of about 200 nsec.

The gamma camera head includes electronic circuitry 40 which receives the signals produced by photomultipliers 38, such signals being hereinafter referred to as input signals associated with interactions of stimuli with the scintillation crystal of the camera head. For each scintillation or light event in the crystal, a group of input signals is supplied to circuitry 40. The amplitude distribution of a group of input signals is a measure of the location in the crystal of the event causing such signals in the crystal.

Circuitry 40 is representative of the conventional electronics in a gamma camera head and includes circuitry 40a which functions to integrate the signals produced by the photomultipliers of the camera head and produces, for each group of input signals, a group of output signals from which the coordinates of a light event can be computed. Circuitry 40a thus processes groups of input signals and produces groups of output signals that represent an interaction of a stimulus with the head of the camera. Depending on the type of components used in electronics 40 and design of the circuitry therein, circuitry 40 will have, for a given camera head, a dead time of $\tau$ sec which represents the time during which the electronics processes a single event and is unavailable to process a succeeding event. Head 36, as thus far described, is entirely conventional in nature.

System 30 also includes coordinate computation circuitry 40b which may be analog or digital in operation for operating on the output signals produced by circuitry 40a for calculating the coordinates of the interaction that is represented by the group of output signals applied to circuitry 40b. The operation of circuitry 40b is conventional in nature and produces the x coordinate, the y coordinate and the so-called z coordinate of each event. The latter represents the total energy of a light event in the crystal and is used to validate the coordinate signals, x, y. That is to say, if the energy signal z lies within a predetermined energy window of a single channel analyzer that is part of the coordinate computation circuitry 40b, then a conclusion is reached that the event causing the coordinates to be generated arose from a primary radiation stimulus interacting with the gamma camera head and not from secondary radiation. In such case, the z signal gates the coordinates x, y into image memory 32 thereby indexing a register at an address in the image memory corresponding to the calculated coordinates. In this way, a record of the event is stored in the image memory. If the z signal lies outside the energy window of the single channel analyzer, then no record in the image memory is made. However, during the collection time of the photons in the crystal and the processing necessary to compute the coordinates and the z signal of the event, the camera cannot process a subsequent event which may be a valid one.

While image memory 32 is shown in the drawing and described above as a digital memory, the present invention is also applicable to an analog-type of memory on which a recording of the representation of the activity distribution of a radiation field can be made. For example, the activity of the field can be recorded on a sheet of photographic film exposed to the screen of a CRT driven by the output of the coordinate computation circuitry. Thus the term "image memory" is intended to comprehend both digital and analog representations of a field and to a recording of such field.

The above described operation of the gamma camera head, the coordinate computation circuitry and the manner of recording a representation of the activity distribution of the field are all well known in the art and entirely conventional. As is well known, circuitry 40 has an efficiency for converting groups of input signals to groups of output signals functionally related to the rate at which the groups of input signals are applied. This is suggested schematically in FIG. 1 above. When the gamma camera described above is used for the purpose of mapping a frame of a dynamically changing radiation field such as is shown at curve 20 in FIG. 2, the portion of image memory 32 designated as 32a will contain the data representing a single frame. Subsequent frames are stored in other locations in image memory 32.

The present invention contemplates the application to the contents of a frame in image memory 32 of a correction factor that compensates for the inefficiency of the analog computation electronics 40 for processing groups of input signals. In order to compute the correction factor, means 34 is utilized. Such means includes synthetic pulse generator 44, responsive to a trigger signal, for injecting synthetic signals into electronics 40. These synthetic signals, in terms of amplitude and shape, resemble input signals produced by photomultipliers 38. Means 34 also includes counter 48 which, as described below, counts the number of synthetic signals processed by electronics 40; and counter 50 which counts the number of times pulse generator 44 is triggered. The ratio of the number of synthetic pulses generated ($N_G$), by pulse generator 44 to the number of synthetic pulses processed ($N_P$) by circuitry 40 is the reciprocal of the efficiency of electronics 40 in converting incoming events to signals applied to coordinate computation circuitry 42.

Figure 4:
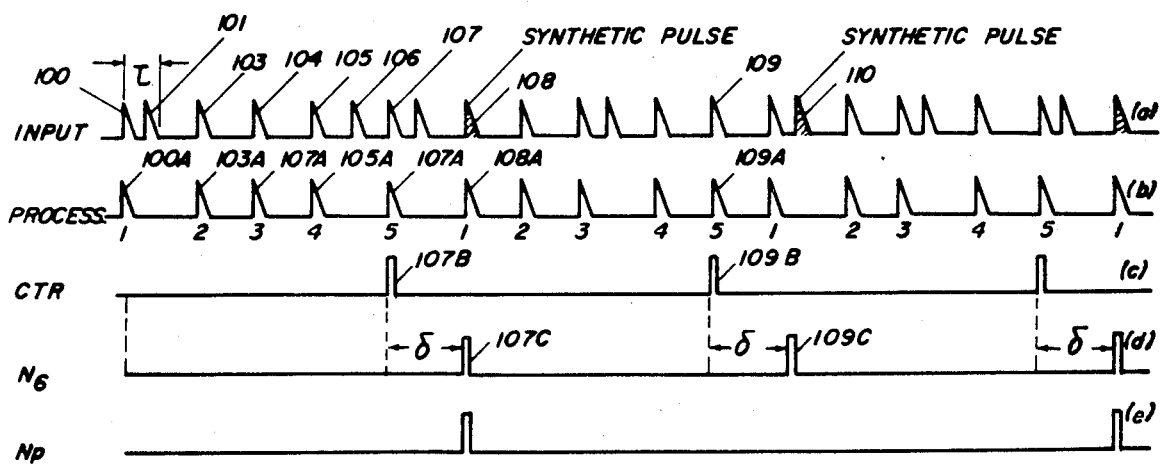
FIG. 4 is a simplified time diagram showing how synthetic pulses are injected into the gamma camera as shown in FIG. 3 and the manner in which the correction factor for the dead time is calculated.

Because describing the operation of means 34, in FIG. 3, reference is made to FIG. 4 which is a simplified showing of the relationship between the groups of input pulses applied to circuitry 40 and the various components of means 34. While FIG. 4 shows every fifth group of output pulses processed by electronics 40 processing a control pulse, it should be understood that this number has been selected only to simplify the drawing and explanation. In any event, each control pulse, after being delayed by a period of time greater than the dead time of electronics 40, will trigger a synthetic pulse generator for the purpose of injecting a synthetic pulse into the input side of electronics 40. Line (a) of FIG. 4 shows input pulses that are applied to electronics 40; and line (b) shows output pulses that are produced by electronics 40. As shown, pulse 101 occurs within the dead time of electronics 40 following pulse 100 with the result that only pulse 100 is processed by electronics 40, which produces output pulse 100A in time coincident with pulse 100. The next group of input pulses 103–105 occur at time intervals greater than the dead time of the camera and are thus processed by electronics 40 which produces output pulses 103A, 104A, 105A in time coincident with the corresponding input pulses. Input pulse 106 occurs subsequent to input pulse 105 within the dead time of the electronics and consequently, pulse 106 is not processed by the electronics. The next input pulsde 107 is processed by electronics 40 and provides output pulse 107A which is the fifth pulse applied to a modulo-5 counter. A decoder associated with the counter produces a control signal 107B when the modulo-5 counter is full. The control signal is delayed and forms a delayed trigger pulse 107C which is applied to the pulse generator. In response, a synthetic pulse 108 is injected into electronics 40. Pulse 108 is processed as pulse 108A and the modulo-5 counter begins to count again. The process is repeated as input pulses are again applied to the electronics and, after input pulse 109 is applied, the fifth output pulse 109A is accumulated in the modulo-5 counter, producing a control signal 109B which is delayed producing trigger pulse 109C thereby triggering the pulse generator which injects synthetic pulse 110 into electronics 40.

The number of synthetic pulses injected into electronics 40, which are shown in processed by the electronics, line (d), and the number of synthetic pulses, which are shown in line (e), can be accumulated in separate counters over the time interval during which a frame is collected in the image memory. The ratio of the contents of these counters will be a measure of the efficiency of the camera and will constitute a correction factor, which when applied to the contents of the map accumulated during the frame-time will correct the map for the dead-time of the camera. This is explained in more detail below.

Referring now to the operation of means 34 in FIG. 3, groups of output signals produced by electronics 40b are counted in counter 52 which, in this instance, is constituted, by a modulo-20 counter because it is the intention to inject a group of synthetic pulses into the input of electronics 40 for every twenty groups of output pulses produced by electronics 40. Decoder 54 produces a control pulse on receipt of each twentieth group of output pulses from electronics 44. The control pulse produced by decoder 54 is applied to delay means 56 which produces a trigger pulse a predetermined time following the control pulse. The trigger pulse is applied to generator 44 which responds by injecting a group of synthetic pulses into electronics 40. The delay time of circuit 56 is set as being greater than the dead time of electronics 40 for the purpose of preventing correlation between the twenty pulses that produce the control pulse by decoder 54, and the group of synthetic pulses produced by generator 44. Because the dead time of circuitry 40 is about 2u seconds, the delay time of circuit 56 can be about 5u seconds. As a consequence, the injection of synthetic pulses is random so far as the groups of input signals are concerned.

Means 34 also includes AND-gate 58 which receives an input each time generator 44 is triggered, and each time a group of output pulses is produced by electronics 40. AND-gate 58 has an output when there is coincidence between the application of a group of synthetic pulses to electronics 40 and the processing of a group of output pulses. Such output thus indicates that a group of synthetic input pulses that have been processed by electronics 40. The output of AND-gate 58 is applied to counter 50 so that the latter counts the number of synthetic pulses that are processed, while counter 48, which is incremented by trigger pulses applied to generator 44, counts the number of synthetic pulses that are applied to electronics 44.

After the lapse of a predetermined period of time, namely the frame time, image memory 32 will contain a map of the radiation field seen by the camera. At this time, the contents of counters 48 and 50 are transferred to correction circuit 60 which computes the correction factor necessary to correct the contents of image memory 32. Such correction factor may be the ratio of the contents of counter 48 to the contents of counter 50. After a given frame has been accumulated in image memory 32, counters 48 and 50 are cleared and the next frame can be accumulated.

In applying the correction factor to a frame map in image memory 32, the contents of each cell in the map is multiplied by the correction factor to define a corrected map which can be stored and then displayed in a conventional manner. Obviously, the correction factor could be the reciprocal of that shown in the drawing with the result that the correction to the map is carried out by dividing the contents of each cell by the correction factor.

The selection of the ratio of the number of synthetic pulses that are injected into the input end of the camera to the number of pulses processed by the camera is somewhat empirical. Such rate should be high enough to be of statistical value in concluding that the ratio of the number of actual pulses processed to the number of actual pulses inputted to the camera behaves like the synthetic pulses. However, the rate should be low enough to insure that the presence of synthetic pulses in the electronics of the head do not interfere significantly with processing the actual pulses. For a map of 64×64 elemental areas, a rate of 5% will be appropriate. That is to say, a synthetic pulse is generated for each 20 processed pulses. In general, the rate will vary from 3 to 10%.

In order to simulate an event, it is preferred for the synthetic pulse generator to inject pulses simultaneously into each of the input lines to electronics 40, there being an input line for each photomultiplier of the array. This arrangement will insure that electronics 40 will treat the group of synthetic pulses exactly like a group of actual pulses. Thus, it is preferred to distribute the amplitudes of each group of synthetic pulses such that the group simulates an event in the crystal adjacent an edge of the field of view or somewhere else outside the medically interesting region of the map produced by the camera.

It is believed that the advantages and improved results furnished by the method and apparatus of the present invention are apparent from the foregoing description of the preferred embodiment of the invention. Various changes and modifications may be made without departing from the spirit and scope of the invention as described in the claims that follow.

We claim:

1. A gamma camera for recording a representation of a frame of a dynamically changing radiation field that produces stimuli comprising:
    (a) a camera head having an array of photodetectors for producing a group of input signals in response to an actual interaction of a stimulus with the head;
    (b) a synthetic signal generator for generating a group of one or more synthetic signals that resemble said input signals and simulate the occurrence of a synthetic interaction of a stimulus with the head at a predetermined location;
    (c) a processing circuit responsive to either a group of input signals or a group of synthetic signals for producing a group of output signals;
    (d) coordinate computation circuitry responsive to a group of output signals of the processing circuit for calculating the coordinates of an interaction, actual or synthetic, causing the output signals;
    (e) means for distinguishing between a real interaction and a synthetic interaction independently of the location of the interaction.

2. A gamma camera according to claim 1 further comprising:
    (a) means for determining the relationship between the number of synthetic interactions and the number of real interactions for calculating a correction factor; and
    (b) means for applying the correction factor to a representation of the field to obtain a corrected representation.

3. A gamma camera according to claim 1 wherein the group of synthetic signals consists of one signal.

4. A gamma camera according to claim 1 wherein the number of synthetic signals in the group of synthetic signals is the same as the number of input signals in the group of input signals.

5. A method for compensating for the dead time of a gamma camera when recording a representation of a dynamically changing radiation field, said gamma camera having a plurality of photodetectors arranged in a predetermined array with respect to a scintillation crystal with which a stimulus from the radiation field interacts to produce a light event which causes the photodetectors to produce a group of input signals that are applied to a processing circuit for producing a representation of the coordinates of the light event, the method comprising:
    (a) simultaneously injecting into the processing circuit a group of synthetic pulses which simulate the group of input signals produced by the photodetectors in response to a light event in the crystal at a particular location;
    (b) determining the percentage of synthetic pulses that are processed by the system for calculating a correction factor; and (c) applying the correction factor to the representation of the field to obtain a corrected representation.

6. A method for compensating for the dead time of a gamma camera having electronic circuitry for recording a representation of a dynamically changing radiation field, comprising:
   (a) injecting into the circuitry groups of synthetic pulses that resemble, in terms of amplitude and shape, groups of input pulses produced in response to the actual interaction of stimuli from the field with the gamma camera at a predetermined location;
   (b) discriminating between groups of said synthetic pulses and groups of said input pulses independently of the location at which said synthetic pulses are injected into the circuitry;
   (c) determining the percentage of synthetic pulses that are processed by the system for calculating a correction factor; and
   (d) applying the correction factor to the representation of the field to obtain a corrected representation.

7. A method according to claim 6 including the steps of:
   (a) processing groups synthetic and input pulses for obtaining groups of processed pulses;
   (b) discriminating a group of synthetic pulses from a group of input pulses by determining the time-coincidence between the generation of a group of synthetic pulses and the occurrence of a group of processed pulses.

8. A method for compensating for the dead time of a gamma camera having a scintillation crystal responsive to radiation stimuli from a dynamically changing radiation field that has a region of clinical interest for producing light events in the crystal, and having electronic circuitry responsive to said light events for computing a representation of the field comprising:
   (a) injecting into the electronic circuitry a train of synthetic pulses which simulate pulses produced by the gamma camera in response to a light event in the crystal at a particular location which is independent of the region of clinical interest;
   (b) determining the percentage of synthetic pulses that are processed by the system to calculate a correction factor; and
   (c) applying the correction factor to the representation of the field.

9. A method for using a gamma camera having a head including an array of photodetectors that produces a group of input pulses in response to an actual interaction of a radiation stimulus with the camera head, said method comprising:
   (a) repetitiously generating groups of synthetic pulses that resemble groups of input pulses and simulate the occurrence of synthetic interactions of stimuli with the head;
   (b) applying said groups of synthetic and input pulses to processing circuitry that produces groups of processed pulses;
   (c) computing the coordinates of both actual and synthetic interactions based on said processed pulses;
   (d) storing a representation of the spatial locations of both actual and synthetic interactions based on the computed coordinates;
   (e) determining whether a group of processed pulses is the result of a group of input pulses or a a group of synthetic pulses;
   (f) computing a correction factor based on the number of groups of processed synthetic pulses relative to the number of groups of generated synthetic pulses; and
   (g) correcting said representation in accordance with said correction factor.

10. A method according to claim 9 wherein the number of groups of generated synthetic pulses is functionally related to the number of groups of input pulses.

11. A method according to claim 10 wherein the determination of whether a group of processed pulses is the result of a group of input pulses or a group of synthetic pulses is based on determining whether the occurrence of a group of processed pulses is in substantially time coincidence with the generation of a group of synthetic pulses.

12. A method according to claim 9 wherein the step of determining whether a group of processed pulses is the result of a group of input pulses or a group of synthetic pulses includes:
   (a) generating a group of synthetic pulses each time a predetermined number of groups of processed pulses occur; and
   (b) determining that a group of processed pulses is the result of a group of synthetic pulses by the time-coincidence between the occurrence of a group of processed pulses and the generation of a group of synthetic pulses.

13. Apparatus for use with a gamma camera having a head including an array of photodetectors that produces a group of input pulses in response to an actual interaction of a radiation stimulus with the head, said apparatus comprising:
   (a) means for generating a group of synthetic pulses that resemble a group of input pulses and simulate the occurrence of a synthetic interaction of a stimulus with the head;
   (b) processing circuitry responsive to groups of input pulses and synthetic pulses for producing groups of processed pulses; and
   (c) means for counting, on a group-by-group basis, the number of groups of processed pulses that result from groups of generated synthetic pulses and for counting the number of groups of synthetic pulses.

14. Apparatus according to claim 13 including:
   (a) means for computing the coordinates of both actual and a group of synthetic interactions based on said processed pulses;
   (b) means for storing a representation of the spatial locations of both actual and a group of synthetic interactions based on the computed coordinates;
   (c) means for computing a correction factor based on the number of groups of processed synthetic pulses relative to the number of groups of generated synthetic pulses; and
   (d) menas for correcting said representation in accordance with said correction factor.

15. Apparatus according to claim 14 including means for computing a correction factor based on the number of groups of synthetic pulses relative to the number of groups of generated synthetic pulses.

16. A method according to claim 13 wherein the number of synthetic pulses in a group is the same as the number of photodetecors in said array.

* * * * *